US00PP13653P29

(12) United States Plant Patent
Osborne

(10) Patent No.: US PP13,653 P2
(45) Date of Patent: Mar. 11, 2003

(54) FERN PLANT NAMED 'CROCODYLLUS'

(76) Inventor: Anthony John Osborne, 63 Butler Drive, Kuranda, Queensland, 4872 (AU)

( * ) Notice: Subject to any disclaimer, the term of this patent is extended or adjusted under 35 U.S.C. 154(b) by 0 days.

(21) Appl. No.: 10/158,963

(22) Filed: May 31, 2002

(51) Int. Cl.[7] ..... A01H 5/00

(52) U.S. Cl. ..... Plt./379
(58) Field of Search ..... Plt./379

*Primary Examiner*—Kent Bell
(74) *Attorney, Agent, or Firm*—C. A. Whealy

(57) ABSTRACT

A new and distinct cultivar of Fern plant named 'Crocodyllus', characterized by its upright and outwardly arching plant habit; numerous fronds; and dense and bushy appearance.

3 Drawing Sheets

BOTANICAL CLASSIFICATION/CULTIVAR DESIGNATION

*Microsorium musifolium* cultivar 'Crocodyllus'.

BACKGROUND OF THE INVENTION

The present Invention relates to a new and distinct cultivar of Fern plant, botanically known as *Microsorium musifolium*, and hereinafter referred to by the cultivar name 'Crocodyllus'.

The new Fern was discovered by the Inventor as a naturally-occurrng whole plant mutation of an unidentified selection of *Microsorium musifolium*, not patented. The cultivar Crocodyllus was selected by the Inventor as a single plant within a population of tissue-cultured plants of the unidentified selection in a controlled environment in Kuranda, Australia.

Asexual reproduction of the new Fern by tissue culture in a controlled environment in Kuranda, Australia since 1998, has shown that the unique features of this new Fern are stable and are reproduced true to type in successive generations.

SUMMARY OF THE INVENTION

The new Fern has not been observed under all possible environmental conditions. The phenotype may vary somewhat with variations in enviroment such as temperature and light intensity without, however, any variance in genotype.

The following characteristics have been repeatedly observed and are determined to be basic characteristics of 'Crocodyllus' and distinguish 'Crocodyllus' as a new and distinct cultivar of Fern:

1. Upright and outwardly arching plant habit.

2. Numerous fronds; dense and bushy appearance.

Plants of the new Fern are most similar to the parent selection; however plants of the new Fern differ from plants of the parent selection in the following characteristics:

1. Plants of the new Fern produce numerous fronds per plant whereas plants of the parent selection produce few fronds per plant.

2. Plants of the new Fern are bushier and denser than plants of the parent selection.

3. Plants of the new Fern grow more rapidly than plants of the parent selection.

4. Plants of the new Fern have smaller rhizomes and smaller fronds than plants of the parent selection.

BRIEF DESCRIPTION OF THE PHOTOGRAPHS

The accompanying colored photographs illustrate the overall appearance of the new Fern, showing the colors as true as it is reasonably possible to obtain in colored reproductions of this type. Colors in the photographs may differ slightly from the color values cited in the detailed botanical description which accurately describe the colors of the new Fern.

The photograph on the first sheet comprises a side perspective view of a typical plant of 'Crocodyllus' grown in a 15.5-cm container.

The photograph on the second sheet is a close-up view of the upper surface of a typical frond of 'Crocodyllus'.

The photograph on the third sheet is a close-up view of the lower surface of a typical frond of 'Crocodyllus'.

DETAILED BOTANICAL DESCRIPTION

The aforementioned photographs and following observations and measurements describe plants grown in Apopka, Fla., in a greenhouse and under conditions which closely approximate those used in commercial practice. Single plants used for the photographs and for the description were grown in 15.5-cm containers and were about ten to eleven months old. Color references are made to The Royal Horticultural Society Colour Chart, 1995 Edition, except where general terms of ordinary dictionary significance are used.

Botanical classification: *Microsorium musifolium* cultivar Crocodyllus.

Parentage: Naturally-occurring whole plant mutation of an unidentified *Microsorium musifolium* selection, not patented.

Propagation:

*Type.*—By tissue culture.

*Time to initiate roots on tissue-culured plants.*—Summer: About 21 days at temperatures of 21° C. Winter: About 30 days at temperatures of 15° C.

*Time to produce a rooted tissue-cultured plant.*—Summer: About 84 days at temperatures of 21° C. Winter: About 84 days at temperatures of 15° C.

*Root description.*—Fine, fibrous; dense; dark brown in color.

*Rhizome description.*—Grows horizontally just below the soil surface. New fronds emerge from multiple growing points on the rhizomes. Rhizomes dark brown in color with short internodes, about 1 to 2 cm.

Plant description:

*General appearance.*—Upright and outwardly arching plant habit; inverted triangular plant shape. Relatively vigorous growth habit and rapid plant growth rate.

*Plant height.*—About 45 to 60 cm.

*Plant diameter or spread.*—About 74 to 85 cm.

*Frond description.*—Shape: Sessile, simple, Variably ovate to somewhat obovate; fertile and sterile fronds similar in form. Apex: Acuminate. Base: Obtuse. Margin: Entire, undulate. Length: About 55 to 65 cm. Width: About 8 to 14 cm. Aspect: Midrib tends to be straight or curved downward towards the apex; undulate. Texture, upper and lower surfaces: Textured dimpled appearance. Venation: Blade is convex between veins on the upper surface giving the leaf a textured dimpled appearance. The midrib protrudes from the upper and lower surfaces. Primary veins on fronds radiate out from the midrib along the length of the frond and have a net-like appearance. Primary veins protrude from the lower surface. Color: Young and fully expanded fronds, upper surface: Greener than, but closest to 146C. Young and fully expanded fronds, lower surface: 147C. Venation, upper surface: Midrib, greener than, but closest to 160C; primary veins, 147A. Venation, lower surface: Midrib, darker and greener than, but closest to 160C; primary veins, 147A. Sori: Arrangement: At distal portion of lower surface of fronds. Shape: Round. Diameter: About 1 to 1.5 cm. Color: 145D.

Disease/pest resistance: Plants of the new Fern have not been observed to resistant to pathogens and pests common to Ferns.

It is claimed:

1. A new and distinct cultivar of Fern plant named 'Crocodyllus', as illustrated and described.

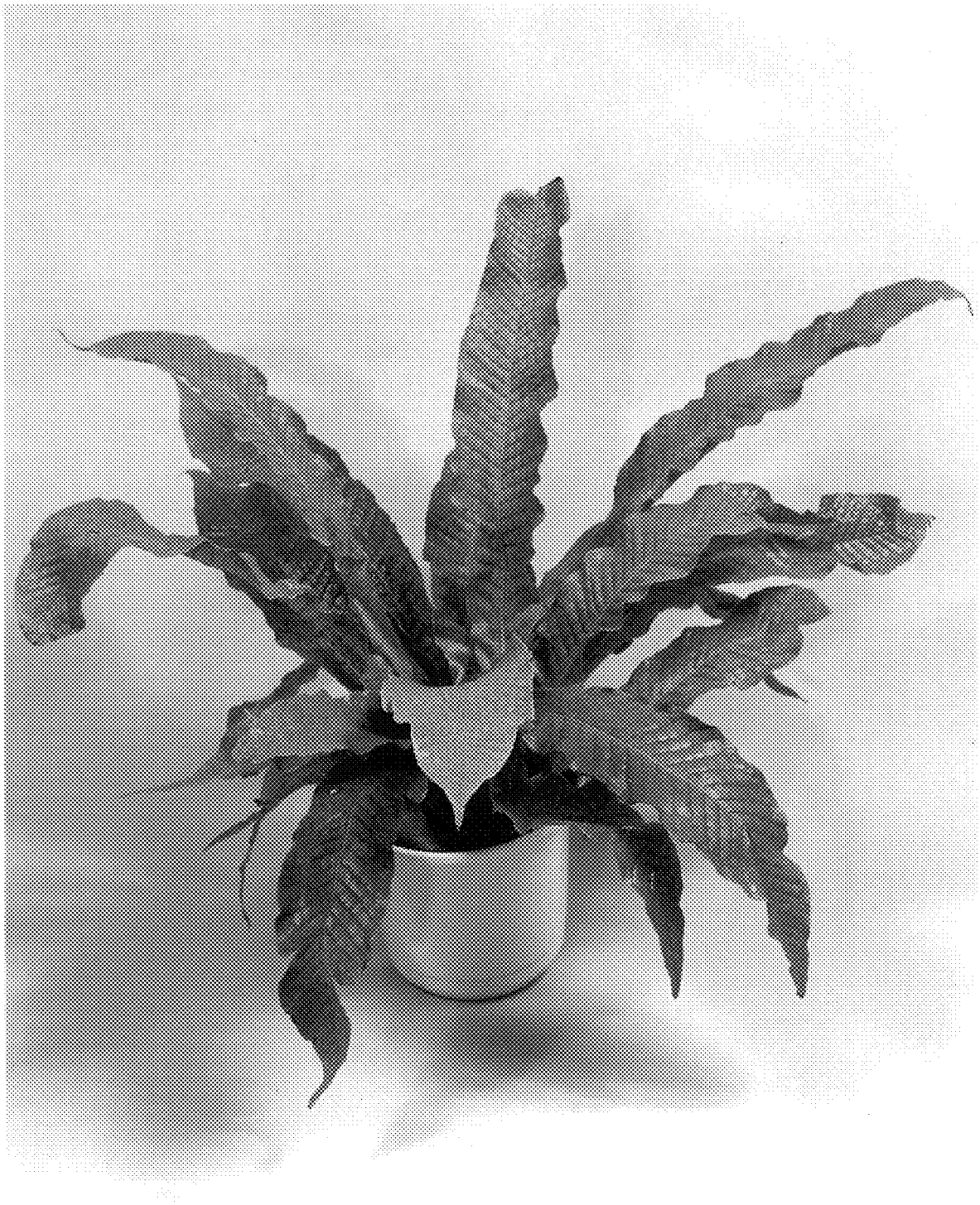

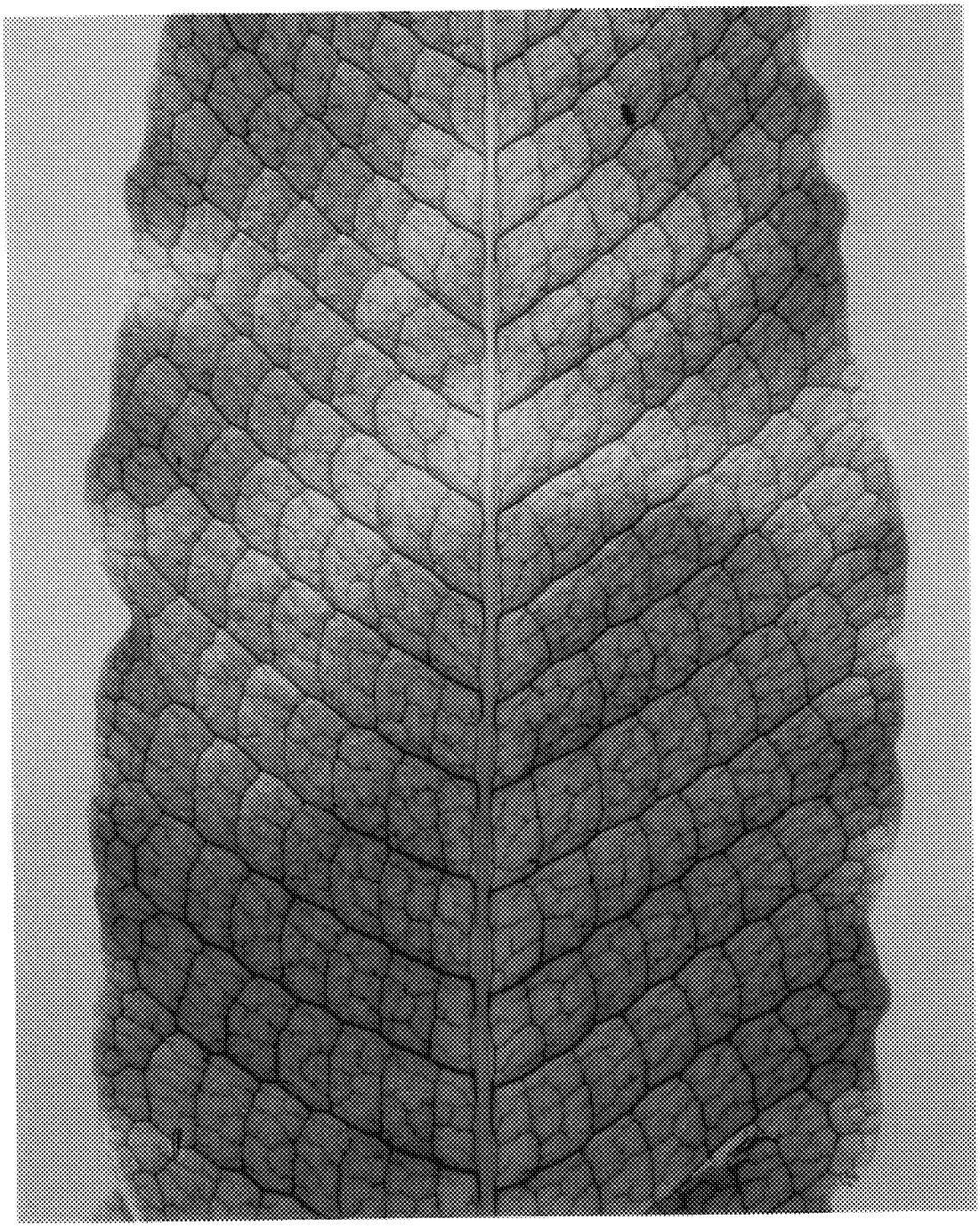

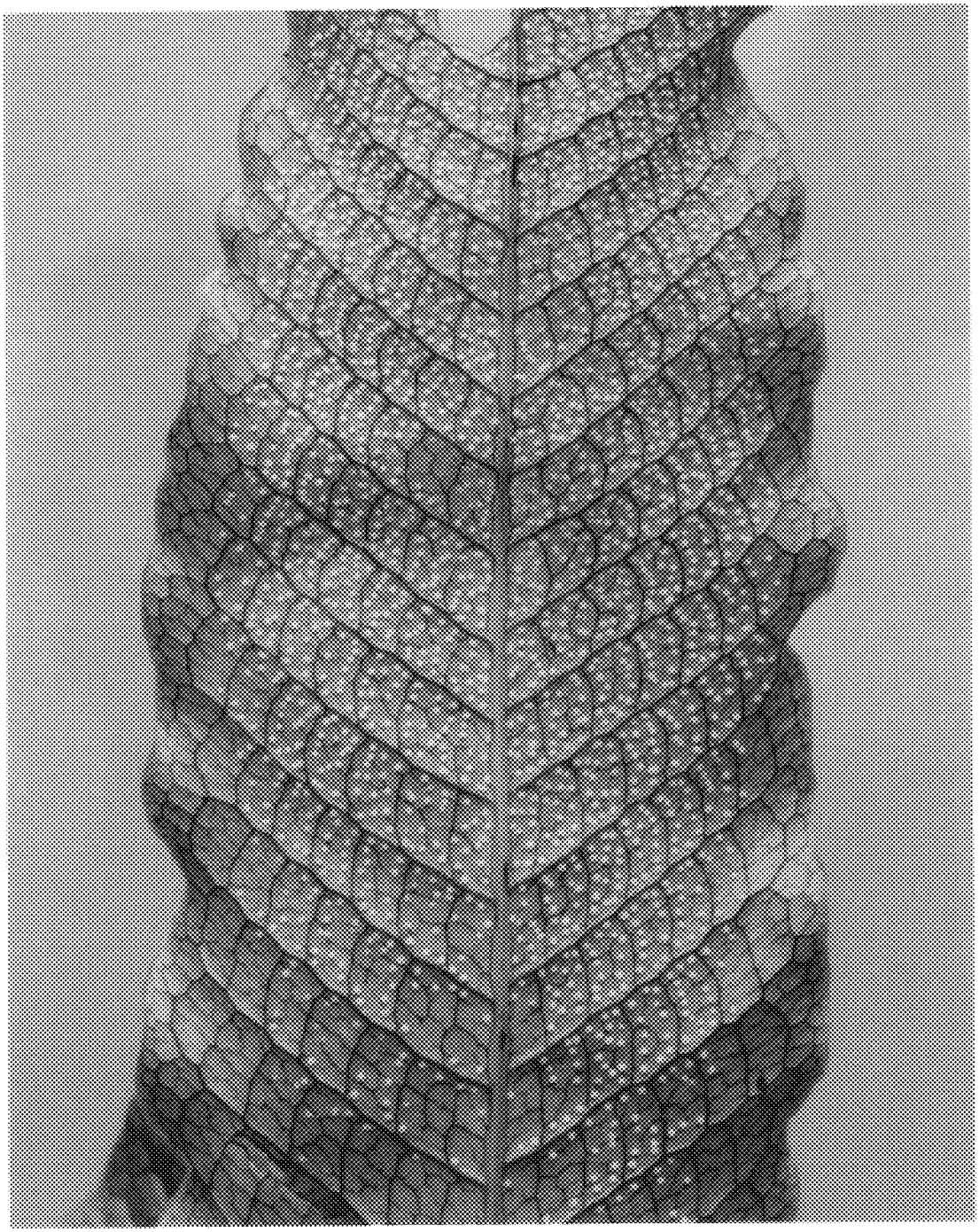

* * * * *